United States Patent [19]

Hussain

[11] Patent Number: 4,965,066
[45] Date of Patent: Oct. 23, 1990

[54] INTRANASAL ADMINISTRATION OF 3,3-DISUBSTITUTED INDOLINES

[75] Inventor: Munir A. Hussain, Wilmington, Del.

[73] Assignee: E. I. Du Pont de Nemours and Company, Wilmington, Del.

[21] Appl. No.: 362,284

[22] Filed: Jun. 6, 1989

[51] Int. Cl.$^5$ ...................... A61K 9/12; A61K 31/175
[52] U.S. Cl. ........................................ 424/45; 514/333
[58] Field of Search ............................ 514/333; 424/45

[56] References Cited

U.S. PATENT DOCUMENTS

| | | | |
|---|---|---|---|
| 4,760,083 | 7/1988 | Myers et al. | 514/333 |
| 4,816,454 | 3/1989 | Zoller et al. | 514/230.5 |
| 4,859,692 | 8/1989 | Bernstein et al. | 514/230.5 |

Primary Examiner—Shep K. Rose

[57] ABSTRACT

There is disclosed intranasal pharmaceutical compositions of 3,3-disubstituted indolines useful for treating cognitive or neurological dysfunction in a mammal. Also disclosed is a method of treating cognitive neurological dysfunction in a mammal comprising administering intranasally to the mammal, the 3,3-disubstituted indolines of formula (I).

25 Claims, No Drawings

INTRANASAL ADMINISTRATION OF 3,3-DISUBSTITUTED INDOLINES

FIELD OF INVENTION

This invention relates to intranasal pharmaceutical compositions and more particularly to such intranasal compositions containing 3,3-disubstituted indolines and methods of using them to treat cognitive deficiencies and/or neurological function deficits and/or mood and/or mental disturbances in mammals.

BACKGROUND OF THE INVENTION

Co-assigned U.S. Pat. No. 4,760,083 issued to Myers et al. on July 26, 1988 discloses 3,3-disubstituted indolines useful for treatment of cognitive deficiencies and/or neurological function deficits and/or mood and/or mental disturbances in a mammal. The disclosure of this patent is incorporated herein by reference. As described therein, the indolines have the formula:

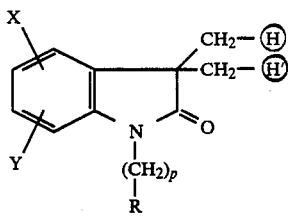
(I)

wherein:
p is 0 or 1;
Z is O or S;
R is $C_1$–$C_{10}$ alkyl, $C_3$–$C_8$ cycloalkyl. 2-pyridyl, 3-pyridyl, 4-pyridyl or

V, W, X, and Y independently are H, halo, $C_1$–$C_3$ alkyl, $OR^1$, $NO_2$, $CF_3$, CN or $NR^2R^2$; $R^1$ and $R^2$ independently are H or $C_1$–$C_3$ alkyl; —(H) and —(H') independently are 6-membered heterocyclic aromatic rings containing at least one nitrogen atom as a part of the ring optionally substituted with one substituent selected from the group $C_1$–$C_3$ alkyl, halo, $OR^1$ or $NR^1R^2$; or an N-oxide or pharmaceutically suitable acid addition salt thereof.

Disclosed in the above identified patent are various dosage forms for the administration of the indoline compounds, however, no nasal dosage form is disclosed. It has been found that intranasal dosing of these compounds improves bioavailability to greater than 50% of the dose administered.

SUMMARY OF THE INVENTION

There is provided a pharmaceutical composition comprising a suitable intranasal pharmaceutical carrier and a compound present in an amount to deliver to a mammal about 0.1 mg/kg to 30 mg/kg, having the formula:

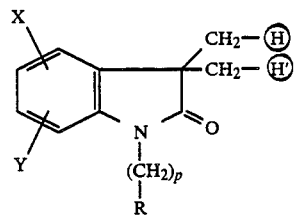
(I)

wherein:
p is 0 or 1;
Z is O or S;
R is $C_1$–$C_{10}$ alkyl, $C_3$–$C_8$ cycloalkyl, 2-pyridyl, 3-pyridyl, 4-pyridyl or

V, W, X, and Y independently are H, halo, $C_1$–$C_3$ alkyl, $OR^1$, $NO_2$, $CF_3$, CN or $NR^2R^2$; $R^1$ and $R^2$ independently are H or $C_1$–$C_3$ alkyl; —(H) and —(H') independently are 6-membered heterocyclic aromatic rings containing at least one nitrogen atom as a part of the ring optionally substituted with one substituent selected from the group $C_1$–$C_3$ alkyl, halo, $OR^1$ or $NR^1R^2$; or a pharmaceutically suitable acid addition salt thereof.

Further provided is a method for treating a cognitive or neurological dysfunction in a mammal by administering intranasally to the mammal a compound of formula (I).

PREFERRED EMBODIMENTS

Preferred compounds for use in the present intranasal compositions are those of formula (I) where:
p is 0; or
Z is 0; or
X and Y are H; or
R is $CH_3$, or m-chlorophenyl; or —(H) and —(H') each pyridyl attached by a ring carbon atoms.

Specifically preferred compounds for use in the present intranasal compositions, for their ability to enhance stimulus-induced acetylcholine release are:
3,3-Bis(2-pyridylmethyl)-1-phenylindolin-2-one;
3,3-Bis(3-pyridylmethyl)-1-phenylindolin-2-one;
3,3-Bis(4-pyridylmethyl)-1-phenylindolin-2-one;
3,3-Bis(4-pyridylmethyl)-1-methylindolin-2-one;
3.3-Bis(4-pyridylmethyl)-1-(3-chlorophenyl)indolin-2-one;
and an N-oxide or pharmaceutically suitable acid addition salt thereof.

DETAILED DESCRIPTION OF THE INVENTION

The compounds of the present invention can be synthesized as disclosed in U.S. Pat. No. 4,760,083 issued to Myers et al. on July 26, 1988 and previously incorporated herein by reference.

The present invention is directed to the delivery of the above compounds intranasally. The active ingredient will ordinarily be present in an amount of about 0.5–95% by weight based on total weight of the composition. The active ingredient can be administered to a mammal at a dosage range of about 0.1 to 30 mg/kg while the preferred dosage range is about 0.1 to 6.0 mg/kg.

Compositions of the active ingredients can be administered intranasally by preparing a suitable formulation of the active ingredient by procedures well known to those skilled in the art. Preferably the formulations are prepared with suitable nontoxic pharmaceutically acceptable ingredients. These ingredients are known to those skilled in the preparation of nasal dosage forms and some of these can be found in REMINGTON'S PHARMACEUTICAL SCIENCES. 17th edition, 1985 a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, jelling agents, or buffering and other stabilizing and solubilizing agents may also be present. Preferably, the nasal dosage form should be isotonic with nasal secretions.

An example of a nasal solution composition of this invention includes:

| Active Drug | 0.02–2 g |
|---|---|
| Sodium Acetate | 0.300 g |
| Methylparaben | 0.100 g |
| Propylparaben | 0.020 g |
| Sodium Chloride | As needed for tonicity |
| Hydrochloric Acid or Sodium Hydroxide | To adjust pH |
| Purified Water | To 100 mL |

The formulation of this invention may be varied to include: (1) other acids and bases to adjust the pH; (2) other tonicity imparting agents such as sorbitol, glycerin and dextrose; (3) other antimicrobial preservatives such as other parahydroxy benzoic acid esters, sorbate, benzoate, propionate, chlorbutanol, phenylethyl alcohol, benzalkonium chloride, and mercurials; (4) other viscosity imparting agents such as sodium carboxymethylcellulose, microcrystalline cellulose, polyvinylpyrrolidone, polyvinyl alcohol and other gums; (5) suitable absorption enhancers; (6) stabilizing agents such as antioxidants, like bisulfite and ascorbate, metal chelating agents such as sodium edetate and drug solubility enhancers such as polyethylene glycols.

The above formulation can be administered as drops, sprays, aerosols or by any other intranasal dosage form. Optionally, the delivery system can be a unit dose delivery system. The volume of solution or suspension delivered per dose can be anywhere from 5 to 400 $\mu$l, and preferably between 50 to 150 $\mu$l. Delivery systems for these various dosage forms can be dropper bottles, plastic squeeze units, atomizers, nebulizers or pharmaceutical aerosols in either unit dose or multiple dose packages.

Examples of nasal compositions of the above compounds which were tested in vivo are set forth below. Parts and percentages are by weight unless otherwise indicated.

EXAMPLES

Bioavailability Studies

Male Lewis rats weighing approximately 300 g were used. All rats were anesthetized with 50 mg/kg pentobarbital (Nembutal commercially available from Abbott) i.p. 3,3 bis(4-pyridylmethyl)-1-phenylindolin-2-one (1') was administered intravenously, orally, and nasally to compare oral and nasal bioavailability. For i.v. administration a dose of the dihydrochloride of compound (1'), herein referred to as compound (1") equivalent to 2 mg/kg of (1') was administered by cardiac puncture in a volume of 1 ml/kg. The oral dose of (1') was 20 mg/kg also administered as (1") in a volume of 1 ml/kg. This dose was administered by gavage. The nasal dose of (1') was administered to rats after surgical isolation of the nasal cavity. The trachea was cannulated to allow free breathing, and a closed tube was inserted anteriorly through the esophagus to block the posterior part of the nasal cavity. The incisive ducts were closed with an adhesive to prevent drainage into the mouth. The dose was administered through the nares with a microliter syringe via polyethylene tubing. The nasal dose of compound (1") was equivalent to 4 mg/ml of the base, and the dosing volume was 0.25 ml/kg, administered through both nares. Serial blood samples ($\sim$0.5 ml) were collected into heparinized test tubes after cutting the tip of the tail. Plasma was separated and frozen until analyzed for Compound (1').

Plasma concentrations of compound (1') were determined by High Performance Liquid Chromatography (HPLC) after solvent extraction. 0.2 ml plasma, 0.1 ml internal standard solution (0.15 mg propranolol HCl/ml water), 0.1 ml of sodium carbonate solution (3.5% in water), and 5 ml ethyl acetate were added to test tubes. The tubes were vortexed for about 5 minutes, and after centrifugation the organic layer was transferred to conical centrifuge tubes to which 0.25 ml of 0.1 N HCl was added. The tubes were vortexed for about 1 minute and after centrifugation the organic phase was removed. Aliquots of the acid were injected onto the HPLC. Separation of compound (1') and the internal standard was achieved at ambient temperature on a 4.6$\times$250 mm cyano column (Zorbax CN. Du Pont) attached to a guard column packed with cyano packing. A liter of mobile phase contained 620 ml of 0.1 M acetate buffer at pH 3.5, 480 ml acetonitrile, 5 ml tetrahydrofuran, and 0.75 g sodium heptanesulfonate. At a flow rate of 1.75 ml/min the retention times of compound (1') and the internal standard were 7.4 and 5.5 minutes respectively. Detection was by ultraviolet (uv) absorbance at 252 nm. The detection limit was 0.12 $\mu$g/ml plasma.

The area under the plasma compound (1') concentration vs. time curve (AUC) from 0 to 3 hr was calculated for each rat (See Table I). Systemic bioavailability after oral and nasal doses was calculated for each rat as the ratio of $AUC^{oral}$ or $^{nasal}/AUC^{iv}$, using the average $AUC^{iv}$ and correcting for the differences in dose. Values are expressed as percentage (%) of dose.

TABLE I

Oral and Nasal Bioavailability (F) of Compound (1') in Rats

| | Dose* | $AUC^{0-3\ hr}$ ($\mu$g hr ml$^{-1}$) | F(% of Dose) | N** |
|---|---|---|---|---|
| I.V. | 2 mg/kg | 1.26 ± 0.09 | 100 | 13 |
| Oral | 20 mg/kg | 1.15 ± 0.24 | 9.1 ± 1.9 | 9 |
| Nasal | 4 mg/kg | 1.34 ± 0.14 | 53.0 ± 5.5 | 5 |

*Dose in terms of free base
**N = number of rats.

EXAMPLE 1

The oral bioavailability of compound (1') averaged about 9.1% of the dose whereas nasal bioavailability of compounds (1') averaged about 53% of the dose (Table 1). In addition to the markedly improved bioavailability seen with intranasal administration, nasal absorption was rapid as evidenced by the maximum plasma concentrations which were attained within 10 minutes of administration of compound (1') intranasally.

Brain uptake studies indicate approximately equal delivery of active compound to the brain by IV and intranasal dosing.

An advantage of the intranasal administration of the compounds of this invention is the improved bioavailability of intranasal dosing as compared to oral dosing (See Table I). Additionally, intranasal dosage forms offer a convenient means of administration.

What is claimed is:

1. A pharmaceutical composition in the form of nasal spray, nasal drops, nasal ointment, nasal gel or an aerosol comprising a suitable intranasal pharmaceutical carrier which is isotonic with nasal secretions and a compound present in an amount to deliver to a mammal about 0.1 mg/kg to 30 mg/kg, said compound having the formula:

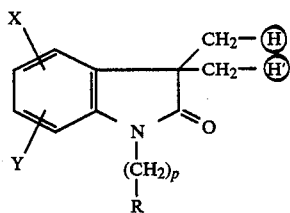

wherein:
p is 0 or 1;
Z is O or S;
R is $C_1$-$C_{10}$ alkyl, $C_3$-$C_8$ cycloalkyl, 2-pyridyl, 3-pyridyl, 4-pyridyl or

V, W, X, and Y independently are H, halo, $C_1$-$C_3$ alkyl, $OR^1$, $NO_2$, $CF_3$, CN or $NR^2R^2$, $R^1$ and $R^2$ independently are H or $C_1$-$C_3$ alkyl; —(H) and —(H') independently are 6-membered heterocyclic aromatic rings containing at least one nitrogen atom as a part of the ring optionally substituted with one substituent selected from the group $C_1$-$C_3$ alkyl, halo, $OR^1$, or $NR^1R^2$; or an oxide or pharmaceutically suitable acid addition salt thereof.

2. An intranasal composition of claim 1 wherein a compound of formula I is present in an amount to deliver about 0.1 mg/kg to 6.0 mg/kg.

3. An intranasal composition of claim 1 wherein p is 0.

4. An intranasal composition of claim 1 wherein Z is O.

5. An intranasal composition of claim 1 wherein each of X and Y is H.

6. An intranasal composition of claim 1 wherein R is $CH_3$, phenyl, or m-chlorophenyl.

7. An intranasal composition of claim 1 wherein each of —(H) and —(H') is pyridyl attached by a ring carbon atom.

8. An intranasal composition of claim 1 wherein: p is 0; Z is O; each of X and Y is H; R is $CH_3$, m-chlorophenyl or phenyl; and each of —(H) and —(H') is pyridyl attached by a ring carbon.

9. An intranasal composition of claim 1 wherein the compound is 3,3-bis(2-pyridylmethyl)-1-phenylindolin-2-one or a pharmaceutically suitable acid addition salt thereof.

10. An intranasal composition of claim 1 wherein the compound is 3,3-bis(3-pyridylmethyl)-1-phenylindolin-2-one or a pharmaceutically suitable acid addition salt thereof.

11. An intranasal composition of claim 1 wherein the compound is 3,3-bis(4-pyridylmethyl)-1-phenylindolin-2-one or a pharmaceutically suitable acid addition salt thereof.

12. An intranasal composition of claim 1 wherein the compound is 3,3-bis(4-pyridylmethyl)-1-methylindolin-2-one or a pharmaceutically suitable acid addition salt thereof.

13. An intranasal composition of claim 1 wherein the compound is 3,3-bis(4-pyridylmethyl)-1-(3-chlorophenyl)indolin-2-one or a pharmaceutically suitable acid addition salt thereof.

14. A method of treatment of cognitive or neurological dysfunction in a mammal comprising administering intranasally, in the form of a nasal drop, nasal spray, nasal ointment, nasal gel or an aerosol to a mammal an effective amount of a compound having the formula:

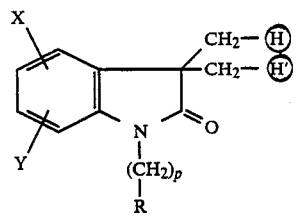

wherein:
p is 0 or 1;
Z is O or S;
R is $C_1$-$C_{10}$ alkyl, $C_3$-$C_8$ cycloalkyl, 2-pyridyl, 3-pyridyl, 4-pyridyl or

V, W, X independently are H, halo, $C_1$-$C_3$ alkyl, $OR^1$, $NO_2$, $CF_3$, CN or $NR^2R^2$;
$R^1$ and $R^2$ independently are H or $C_1$-$C_3$ alkyl;
—(H) and —(H') independently are 6-membered heterocyclic aromatic rings containing at least one nitrogen atom as a part of the ring optionally substituted with one substituent selected from the group $C_1$-$C_3$ alkyl, halo, $OR^1$, or $NR^1R^2$; or an oxide or pharmaceutically suitable acid addition salt thereof.

15. A method of treatment of claim 14 wherein p is 0.

16. A method of treatment of claim 14 wherein Z is O.

17. A method of treatment of claim 14 wherein each of X and Y is H.

18. A method of treatment of claim 14 wherein R is $CH_3$, phenyl, or m-chlorophenyl.

19. A method of treatment of claim 14 wherein each of —(H) and —(H') is pyridyl attached by a ring carbon atom.

20. A method of treatment of claim 14 wherein
p is 0; Z is O; each of X and Y is H; R is CH$_3$, m-chlorophenyl or phenyl; and each of —(H) and —(H') is pyridyl attached by a ring carbon.

21. A method of treatment of claim 14 wherein the compound is 3,3-bis(2-pyridylmethyl)-1-phenylindolin-2-one or a pharmaceutically suitable acid addition salt thereof.

22. A method of treatment of claim 14 wherein the compound is 3,3-bis(3-pyridylmethyl)-1-phenylindolin-2-one or a pharmaceutically suitable acid addition salt thereof.

23. A method of treatment of claim 14 wherein the compound is 3,3-bis(4-pyridylmethyl)-1-phenylindolin-2-one or a pharmaceutically suitable acid addition salt thereof.

24. A method of treatment of claim 14 wherein the compound is 3,3-bis(4-pyridylmethyl)-1-methylindolin-2-one or a pharmaceutically suitable acid addition salt thereof.

25. A method of treatment of claim 14 wherein the compound is 3,3-bis(4-pyridylmethyl)-1-(3-chlorophenyl)indolin-2-one or a pharmaceutically suitable acid addition salt thereof.

* * * * *